(12) United States Patent
Beelen et al.

(10) Patent No.: US 11,903,660 B2
(45) Date of Patent: *Feb. 20, 2024

(54) SURGICAL ROBOTIC SYSTEM AND CONTROL OF SURGICAL ROBOTIC SYSTEM

(71) Applicant: PRECEYES B.V., Eindhoven (NL)

(72) Inventors: Maarten Joannes Beelen, 's-Hertogenbosch (NL); Gerrit Jacobus Lambertus Naus, Eindhoven (NL); Hildebert Christiaan Matthijs Meenink, Steenderen (NL); Marc Joseph Dominique De Smet, Mont sur Lausanne (CH)

(73) Assignee: PRECEYES B.V., Eindhoven (NL)

( * ) Notice: Subject to any disclaimer, the term of this patent is extended or adjusted under 35 U.S.C. 154(b) by 112 days.

This patent is subject to a terminal disclaimer.

(21) Appl. No.: 17/236,958

(22) Filed: Apr. 21, 2021

(65) Prior Publication Data

US 2021/0236219 A1 Aug. 5, 2021

Related U.S. Application Data

(63) Continuation of application No. 16/432,379, filed on Jun. 5, 2019, now Pat. No. 11,013,565, which is a (Continued)

(30) Foreign Application Priority Data

Aug. 26, 2014 (NL) ...................................... 2013369

(51) Int. Cl.
*A61B 17/00* (2006.01)
*A61B 34/30* (2016.01)
(Continued)

(52) U.S. Cl.
CPC ........ *A61B 34/30* (2016.02); *A61B 17/00234* (2013.01); *A61B 34/25* (2016.02);
(Continued)

(58) Field of Classification Search
CPC . B25J 3/04; B25J 9/104; B25J 9/1676; G05B 2219/39082; A61B 34/30;
(Continued)

(56) References Cited

U.S. PATENT DOCUMENTS 7,725,214 B2   5/2010   Diolaiti
8,010,180 B2   8/2011   Quaid et al.
(Continued)

FOREIGN PATENT DOCUMENTS

KR   20140008244 A   1/2014

OTHER PUBLICATIONS

International Search Report and Written Opinion issued in International Application No. PCT/EP2015/069372 (in English).

*Primary Examiner* — Dalena Tran
(74) *Attorney, Agent, or Firm* — Whitestone Law, PLLC

(57) ABSTRACT

Some embodiments are directed to a surgical robotic system for use in a surgical procedure, including a surgical arm having a movable arm part for mounting of a surgical instrument having at least one degree-of-freedom to enable longitudinal movement of the surgical instrument towards a surgical target. Some other embodiments are directed to a human machine interface for receiving positioning commands from a human operator for controlling the longitudinal movement of the surgical instrument, and an actuator configured for actuating the movable arm part to effect the longitudinal movement of the surgical instrument, and controlled by a processor in accordance with the positioning commands and a virtual bound. The virtual bound establishes a transition in the control of the longitudinal move- (Continued)

ment of the surgical instrument in a direction towards the surgical target. The virtual bound is determined, during use of the surgical robotic system, based on the positioning commands.

19 Claims, 10 Drawing Sheets

Related U.S. Application Data continuation of application No. 15/506,519, filed as application No. PCT/EP2015/069372 on Aug. 24, 2015, now Pat. No. 10,350,014.

(51) Int. Cl.
  *B25J 9/16* (2006.01)
  *A61B 34/00* (2016.01)
  *A61B 90/00* (2016.01)

(52) U.S. Cl.
  CPC .............. *A61B 34/74* (2016.02); *A61B 34/77* (2016.02); *B25J 9/1676* (2013.01); *A61B 90/03* (2016.02); *A61B 2017/00203* (2013.01); *A61B 2017/00207* (2013.01); *A61B 2017/00216* (2013.01); *A61B 2017/00973* (2013.01); *A61B 2034/742* (2016.02); *A61B 2034/743* (2016.02); *A61B 2034/744* (2016.02); *A61B 2090/062* (2016.02); *A61B 2090/08021* (2016.02); *G05B 2219/39082* (2013.01)

(58) Field of Classification Search
  CPC ... A61B 34/25; A61B 34/74; A61B 17/00234; A61B 2034/742; A61B 2034/743; A61B 2034/744; A61B 2017/00203; A61B 2017/00973
  USPC .... 700/245, 258, 259, 264; 606/1, 130, 170; 901/2, 19, 27; 600/117, 130, 424, 229; 318/568.11, 568.13, 568.16, 568.2
  See application file for complete search history.

(56) References Cited

U.S. PATENT DOCUMENTS

| | | | |
|---|---|---|---|
| 9,999,751 B2 * | 6/2018 | Pacheco | A61B 34/30 |
| 11,207,064 B2 * | 12/2021 | Shelton, IV | A61B 34/71 |
| 11,291,441 B2 * | 4/2022 | Giordano | A61B 17/320092 |
| 11,504,116 B2 * | 11/2022 | Schmid | A61B 17/07207 |
| 2002/0143319 A1 | 10/2002 | Brock | |
| 2007/0144298 A1 | 6/2007 | Miller | |
| 2007/0265638 A1 | 11/2007 | Lipow et al. | |
| 2008/0086080 A1 | 4/2008 | Mastri et al. | |
| 2009/0178943 A1 | 7/2009 | Oostman, Jr. et al. | |
| 2011/0106102 A1 | 5/2011 | Balicki et al. | |
| 2011/0118872 A1 | 5/2011 | Ortmaier et al. | |
| 2012/0158011 A1 | 6/2012 | Sandhu et al. | |
| 2013/0338679 A1 | 12/2013 | Rosielle et al. | |
| 2014/0052150 A1 | 2/2014 | Taylor et al. | |
| 2017/0252113 A1 | 9/2017 | Beelen et al. | |

* cited by examiner

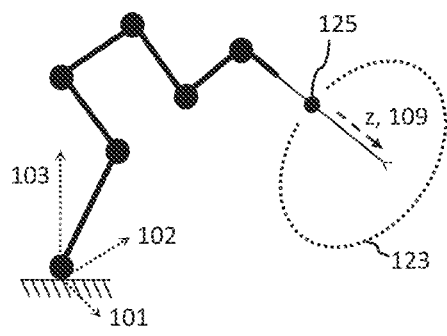
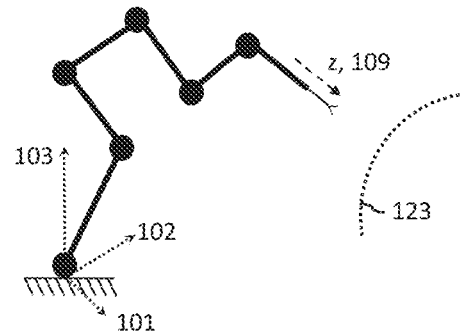
Fig. 5                    Fig. 6
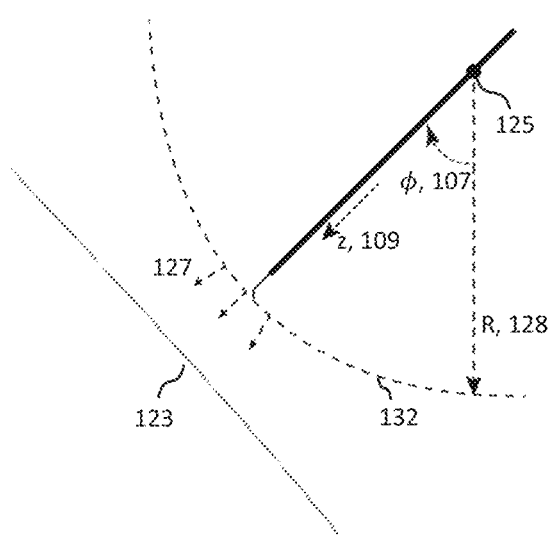
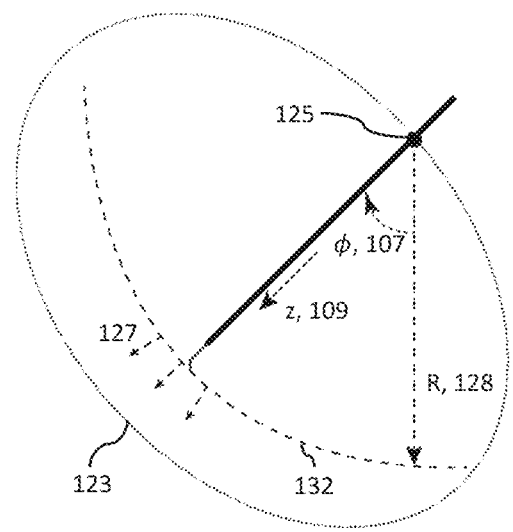
Fig. 7                    Fig. 8

SURGICAL ROBOTIC SYSTEM AND CONTROL OF SURGICAL ROBOTIC SYSTEM

CROSS REFERENCE TO RELATED APPLICATION(S)

This application claims priority to and is a continuation patent application of U.S. patent application Ser. No. 16/432,379 filed on Jun. 5, 2019 for which a Notice of Allowance was issued on Jan. 22, 2021, which is a continuation patent application of U.S. patent application Ser. No. 15/506,519 filed on Feb. 24, 2017 and issued on Jul. 16, 2019 as U.S. Pat. No. 10,350,014, which is a national phase filing under 35 C.F.R. § 371 of and claims priority to International Patent Application No. PCT/EP2015/069372 filed on Aug. 24, 2015, claims the priority of Netherlands patent application 2013369 filed on Aug. 26, 2014 the contents of each of which are incorporated herein by reference in their entireties.

FIELD OF THE INVENTION

The invention relates to a surgical robotic system for use in a surgical procedure. The invention further relates to a method for controlling a surgical robotic system during use in a surgical procedure, and to a computer program product comprising instructions for causing a processor system to perform the method.

BACKGROUND ART

Surgical procedures increasingly involve the use of surgical robotic systems. Rather than operating entirely autonomously, such surgical robotic systems are typically at least in part under the control of a human operator, for example, to control the movement of a surgical instrument mounted to a surgical arm of the surgical robotic system. As such, surgical robotic systems may assist the human operator in performing a surgical procedure.

For that purpose, a surgical robotic system may be provided with a surgical arm which comprises a movable arm part, with the movable arm part comprising an instrument connector for mounting of a surgical instrument. Accordingly, the surgical instrument may be positioned by the surgical arm. A human machine interface may be provided for receiving positioning commands from a human operator for controlling the movement of the surgical instrument. An actuator may be provided for actuating the movable arm part to effect the movement of the surgical instrument in accordance with the positioning commands provided by the human operator. Examples of this approach may be found in the field of tele-operation, where a human operator may operate a master device, e.g., a motion controller, to provide positioning commands for a slave device, e.g., the aforementioned surgical arm.

Surgical robotic systems of the above type are known per se.

For example, US2013338679 A1 describes a surgical robot for performing minimally invasive surgery, comprising a surgical arm, wherein said surgical arm has a fixed surgical arm part and a movable surgical arm part which is movable with respect to said fixed surgical arm part. The surgical arm further comprises a surgical instrument mounted at said movable arm part. A manipulation arm is pivotally engaged with the second engagement point of the fixed surgical arm part using one end of the manipulation arm. It is said that a manipulation control and driving means could be used for controlling the manipulation arm.

The movement of the surgical instrument may be in a longitudinal direction, e.g., along the longitudinal axis of the surgical instrument. This direction is also referred to as the longitudinal axial direction, or in short the axial direction. Such longitudinal movement allows the surgical instrument to be moved towards a surgical target within an interior, or on a surface of an exterior of a patient. Accordingly, the surgical instrument may be used to modify (biological) tissue near the surgical target, to deliver an agent to the surgical target, etc. Examples of such surgical instruments include, but are not limited to, forceps, mechanical cutters, coagulation cutters, scissors, injection needles, sealing devices, etc.

SUMMARY OF THE INVENTION

A problem of the longitudinal movement of a surgical instrument towards a surgical target is that such movement, when insufficiently controlled, may pose a risk. For example, if a surgical target is located on a surface of an organ, an uncontrolled movement towards the surgical target may accidentally puncture the surface.

One of the objects of the invention is to obtain a surgical robotic system and/or method for controlling a surgical robotic system which enables the longitudinal movement of a surgical instrument which is mounted to the surgical robotic system to be better controlled.

A first aspect of the invention provides a surgical robotic system for use in a surgical procedure, comprising:
  a surgical arm comprising a movable arm part, the movable arm part comprising an instrument connector for mounting of a surgical instrument, the surgical instrument having a longitudinal axis, the movable arm part having at least one degree-of-freedom to enable longitudinal movement of the surgical instrument along the longitudinal axis of the surgical instrument towards a surgical target;
  a human machine interface for receiving positioning commands from a human operator for controlling the longitudinal movement of the surgical instrument;
  an actuator configured and arranged for actuating the movable arm part to effect the longitudinal movement of the surgical instrument;
  a processor configured for controlling the actuator in accordance with the positioning commands and a virtual bound, the virtual bound establishing a transition in the control of the longitudinal movement of the surgical instrument in a direction towards the surgical target, and wherein the processor is further configured for, during use, determining the virtual bound based on the positioning commands.

In a further aspect of the invention, a method is provided for controlling a surgical robotic system during use in a surgical procedure, the surgical robotic system comprising a surgical arm, the surgical arm comprising a movable arm part, the movable arm part comprising an instrument connector for mounting of a surgical instrument, the surgical instrument having a longitudinal axis, the movable arm part having at least one degree-of-freedom to enable longitudinal movement of the surgical instrument along the longitudinal axis of the surgical instrument towards a surgical target, the method comprising:
  receiving positioning commands from a human operator for controlling the longitudinal movement of the surgical instrument;

actuating the movable arm part to effect the longitudinal movement of the surgical instrument;

controlling said actuating in accordance with the positioning commands and a virtual bound, the virtual bound establishing a transition in the control of the longitudinal movement of the surgical instrument in a direction towards the surgical target;

the method further comprising:

during use of the surgical robotic system in the surgical procedure, determining the virtual bound based on the positioning commands.

In a further aspect of the invention, a computer program product is provided comprising instructions for causing a processor system to perform the method.

The above aspects of the invention involve a surgical robotic system which comprises a surgical arm. The surgical arm comprises a movable arm part, with the movable arm part comprising an instrument connector for mounting of a surgical instrument. The surgical instrument has a longitudinal axis, typically passing through a tip of the surgical instrument. The movable arm part has at least one Degree-of-Freedom (DoF) to enable longitudinal movement of the surgical instrument along the longitudinal axis of the surgical instrument towards a surgical target. It is noted that the movable arm part may have exactly one DoF aligned with the longitudinal axis of the surgical instrument to enable said longitudinal movement. However, the movable arm part may also have multiple DoFs enabling said longitudinal movement yet without any of the DoFs having to be individually aligned with the longitudinal axis. It is noted that surgical arms having the functionality described in this paragraph are known per se from the field of medical robotics, and also known as instrument manipulators, robotic arms, surgical robot slave devices, etc.

A human machine interface is provided for receiving positioning commands from a human operator for controlling the longitudinal movement of the surgical instrument. In addition, an actuator is provided for actuating the movable arm part to effect the longitudinal movement of the surgical instrument. Another term for actuator is driving mechanism. A processor is provided for controlling the actuator in accordance with the positioning commands. As such, the processor may control the actuation of the movable arm part based on the positioning commands, for example, to effect a desired longitudinal movement of the surgical instrument as indicated by the positioning commands. However, the processor may adjust the control of the actuator based on a virtual bound. Namely, the virtual bound may establish a transition in the control of the longitudinal movement of the surgical instrument in a direction towards the surgical target. Here, the term 'virtual bound' may refer to a data representation of a bound in physical space, e.g., a position, a line or a contour. Moreover, the term 'longitudinal movement towards the surgical target' refers to an advancing movement of the surgical instrument rather than a retracting movement of the surgical instrument, and as such, refers to a movement in the general direction of the surgical target. The virtual bound may cause the processor to transition in control behavior when crossing the virtual bound, and may thereby effectively serve to divide physical space, e.g., the workspace of the surgical robotic system, in different zones. For example, the virtual bound may divide the physical space in a first zone and a second zone, with the second zone comprising the surgical target, which may be associated with a higher risk. The processor may control the actuator differently for positioning commands representing longitudinal movement of the surgical instrument in, and/or in the direction of, the second zone than those representing longitudinal movement in, and/or in the direction of, the first zone.

The processor determines the virtual bound based on the positioning commands during use of the surgical robotic system. As such, the virtual bound may be determined at least in part by the human operator itself, namely from positioning commands which the human operator provides for controlling the longitudinal movement of the surgical instrument.

By applying a virtual bound in the above described manner, the human operator may be provided with safer and/or more accurate control over the surgical instrument in the vicinity of a surgical target. Conversely, away from the surgical target, the safer and/or more accurate control may be deliberately dispensed with to allow faster movement of the surgical instrument. For example, the virtual bound may be used to disallow or dampen longitudinal movement of the surgical instrument towards the surgical target past the virtual bound. At the same time, the inventors have recognized that there is a need to determine the virtual bound without necessarily having to rely on sensor data which is indicative of a distance towards the surgical target. Namely, the surgical robotic system may lack such a sensor, or if a sensor is provided, the sensor data may not always be reliable, etc. However, the inventors have recognized that the positioning commands provided by the human operator are indicative of where a virtual bound is to be suitably (re)positioned. As such, the control behavior of the human operator, as represented by the positioning commands, may be used in determining the position of the virtual bound. Advantageously, it is not needed to rely on sensor data, or sensor data alone, to determine a virtual bound. Rather, the processor may determine the virtual bound based on the positioning commands.

Optionally, the processor may be configured for i) in controlling the actuator, allowing longitudinal movement of the surgical instrument towards the surgical target past the virtual bound, subject to a positioning command being of a selected type, and ii) updating the virtual bound based on a new furthest positioning of the surgical instrument. For example, certain types of positioning commands may be considered 'safe' and thereby may cause the processor to, in addition to longitudinally moving the surgical instrument, also re-position the virtual bound. For example, positioning commands provided using a particular input modality or input mode may be considered as 'safe' or 'safer' than positioning commands provided using other input modalities or input modes. Here, the term 'furthest positioning' refers to a positioning that is considered to by the processor to represent a furthest positioning in accordance with a function. The function may define a virtual volume, with the positioning of the surgical instrument, as determined based from, e.g., the positioning commands, determining a size of the virtual volume, and the furthest positioning being the one which maximizes the size of the virtual volume. The virtual volume may have a predetermined geometry, e.g., corresponding to the general shape of the anatomical structure which comprises the surgical target.

Optionally, the processor may be configured for controlling the actuator to always allow longitudinal movement of the surgical instrument away from the surgical target. Such longitudinal movement may be considered as 'safe' and thus generally allowed.

It will be appreciated by those skilled in the art that two or more of the above-mentioned embodiments, implementations, and/or aspects of the invention may be combined in any way deemed useful.

Modifications and variations of the method and/or the computer program product, which correspond to the described modifications and variations of the surgical robotic system, can be carried out by a person skilled in the art on the basis of the present description.

The invention is defined in the independent claims or clauses. Advantageous yet optional embodiments are defined in the dependent claims or clauses.

BRIEF DESCRIPTION OF THE DRAWINGS

These and other aspects of the invention are apparent from and will be elucidated with reference to the embodiments described hereinafter. In the drawings.

FIG. 5 shows a joint diagram illustrating the kinematics of a surgical arm having six revolutionary DoFs, thereby enabling a remote center of motion and a longitudinal movement of the surgical instrument towards a surgical target;

FIG. 6 shows a joint diagram illustrating the kinematics of a surgical arm in relation to a surgical target which may be located on an exterior of a patient;

FIG. 7 shows a spherical virtual bound being determined based on a furthest positioning of the surgical instrument as established by a human operator during surgery on a surface of an exterior of a patient;

FIG. 8 shows a spherical virtual bound being determined based on a furthest positioning of the surgical instrument as established by a human operator during minimally invasive surgery in a cavity of an organ in an interior of the patient;

Figure 1:
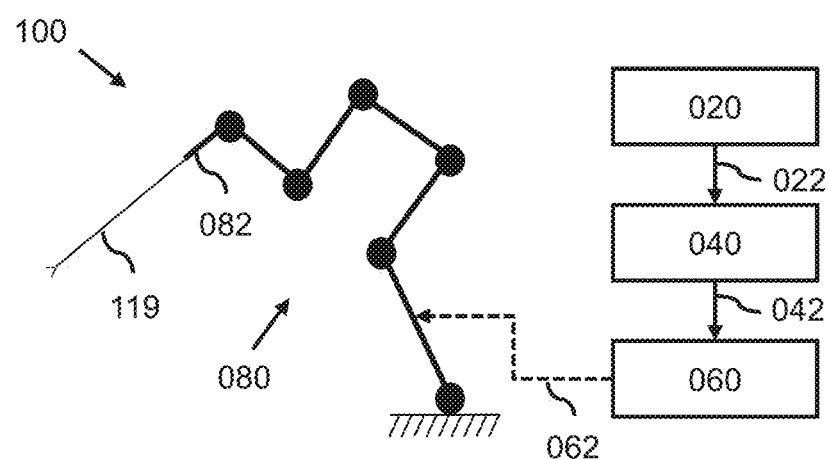
FIG. 1 shows a schematic representation of a surgical robotic system.

It should be noted that items which have the same reference numbers in different figures, have the same structural features and the same functions, or are the same signals. Where the function and/or structure of such an item has been explained, there is no necessity for repeated explanation thereof in the detailed description.

LIST OF REFERENCE NUMERALS

The following list of reference numerals is provided for aiding the interpretation of the drawings and shall not be construed as limiting the claims or clauses.

020 Human machine interface
022 Positioning commands
040 Processor
042 Actuation commands
060 Actuator
062 Actuation of surgical arm
080 Surgical arm
082 Movable arm part
100 Surgical robotic system
101 $\vec{e}_1$, axis of a Cartesian coordinate system
102 $\vec{e}_y$, axis of a Cartesian coordinate system
103 $\vec{e}_z$, axis of a Cartesian coordinate system
104 $\vec{e}_x$, axis of coordinate system fixed to the instrument tip, orthogonal to the instrument longitudinal axis
105 $\vec{e}_y$, axis of coordinate system fixed to the instrument tip, orthogonal to the instrument longitudinal axis
106 $\vec{e}_z$, axis of a Cartesian coordinate system, aligned with the instrument longitudinal axis
107 $\phi$, rotation of surgical instrument, laterally displacing its tip
108 $\psi$, rotation of surgical instrument, laterally displacing its tip
109 z, longitudinal (along its longitudinal axis) translation of surgical instrument, or penetration direction, or advancing direction
110 $\theta$, rotation of surgical instrument around its longitudinal axis
111 $\Phi$ rotational DoF of a movable arm part
112 $\Psi$, rotational DoF of a movable arm part
113 $Z_m$, translational DoF of a movable arm part
114 $\Theta$, rotational DoF of a movable arm part
115 $\Phi_m$, rotational DoF of motion controller
116 $\Psi_m$, rotational DoF of motion controller
117 $Z_m$, translational DoF of motion controller
118 $\Theta_m$, rotational DoF of motion controller
119 Surgical instrument
120 Data points
121 Algebraic geometry for the virtual bound
122 Surgical instrument tip 123 Surgical target
124 Trocar
125 Remote center of motion (RCM)
126 Button on motion controller gripper
127 Repositioning, expansion or deformation of the virtual bound
128 Radius R
129 Length L
130 ϕ=0 line
131 Microscope for vision through pupil
132 Virtual bound
133 Virtual bound at time $t_1$
134 Virtual bound at time $t_2$
135 Virtual bound at time $t_3$
136 Instrument tip at time $t_1$
137 Instrument tip at time $t_2$
138 Instrument tip at time $t_3$
139 Zone A
140 Zone B
143 Zone B at time $t_2$
146 Motion controller
147 Motion controller at time $t_1$
148 Motion controller at time $t_2$
149 Motion controller gripper
151 Increase virtual bound with 50 μm using foot pedal
152 Motion controller displacement $x_m$
153 Surgical instrument displacement $x_s$
154 Velocity mode boundary
156 Motion controller workspace
157 Pushing of the motion controller past the velocity mode boundary
158 Zone of no velocity mode
161 Retract of surgical instrument; longitudinal translation in negative z direction
162 Radius $R_1$ at time $t_1$
163 Radius $R_2$ at time $t_2$
164 Surgical instrument velocity $v_s$
166 Longitudinal distance to virtual bound
167 Scaling function 1 for α
168 Scaling function 2
169 Cut-off frequency (Hz)
170 Retraction instrument in z direction
171 Longitudinal distance between instrument tip and surgical target
172 Numerical model for the virtual bound
200 A method for controlling a surgical robotic system
210 Receiving positioning commands
220 Determining the virtual bound
230 Controlling the actuating
240 Actuating the movable arm part
250 Non-transitory program code
260 Computer readable medium

DETAILED DESCRIPTION OF EMBODIMENTS

FIG. 1 schematically shows a surgical robotic system 100 for use in a surgical procedure. The surgical robotic system 100 comprises a surgical arm 080. The surgical arm 080 comprises a movable arm part 082, with the movable arm part comprising an instrument connector for mounting of a surgical instrument 119. FIG. 1 shows the surgical instrument 119 having been mounted to the instrument connector (for sake of simplicity, the instrument connector is not separately shown in FIG. 1). The movable arm part 082 has at least one DoF to enable longitudinal movement of the surgical instrument towards a surgical target. Here, longitudinal movement refers to a movement of the surgical instrument 119 along its longitudinal axis (for sake of simplicity, the longitudinal axis is not separately shown in FIG. 1).

The surgical robotic system 100 further comprises a human machine interface 020 for receiving positioning commands 022 from a human operator for controlling the longitudinal movement of the surgical instrument. Examples of human machine interfaces include, but are not limited to, a keyboard, a mouse, a touch-sensitive surface, a joystick, a foot pedal. The human machine interface may employ any suitable input modality, such as touch, push-actions, voice commands, eye movements, etc. The surgical robotic system 100 further comprises an actuator 060 configured and arranged for actuating the movable arm part to effect the longitudinal movement of the surgical instrument. The actuator 060 may be any suitable actuator, e.g., from the field of surgical robots, or from the more general field of actuators. In particular, the actuator may be one of a plurality of actuators which together provide the actuation of the movable arm part 060 along the at least one degree-of-freedom (DoF). Namely, the surgical robotic system 100 may comprise a plurality of actuators, e.g., to provide actuation along multiple DoF. As such, it will be appreciated that any reference to a configuration of the actuator 080 may be understood as referring to a (joint) configuration of such a plurality of actuators. FIG. 1 shows the actuation of surgical arm 080 schematically, namely as a dashed line 062. It is noted that, although shown separately of the surgical arm 080, the actuator 060 may be integrated into, or mounted to, the surgical arm 080.

The surgical robotic system 100 further comprises a processor 040 configured for controlling the actuator in accordance with the positioning commands and a virtual bound. For that purpose, the processor 040 is shown to receive the positioning commands 022 from the human machine interface 020 and provide actuation commands 042 to the actuator 060. Here, the virtual bound establishes a transition in the control of the longitudinal movement of the surgical instrument in a direction towards the surgical target. The processor 040 may determine the virtual bound based on the positioning commands during use of the surgical robotic system 100. Having determined the virtual bound, the processor may control the actuator to, e.g., disallow or dampen longitudinal movement of the surgical instrument towards the surgical target past the virtual bound. However, other uses of the virtual bound are equally conceivable, as will be elucidated in reference to FIGS. 16-20.

Figure 2:
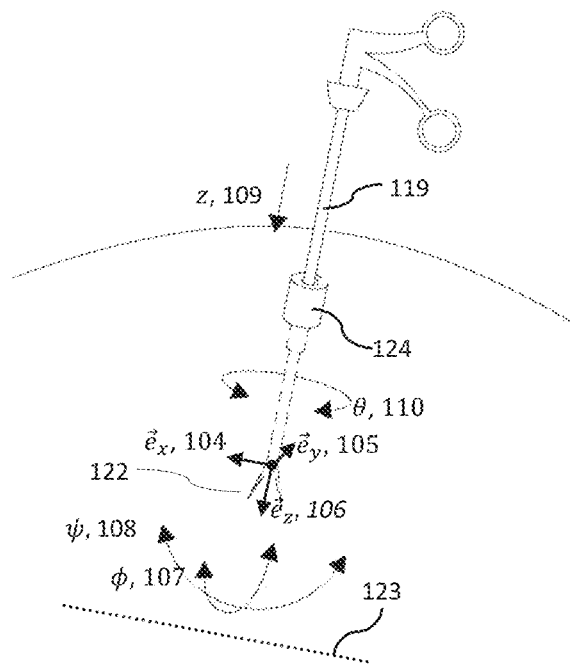
FIG. 2 shows a surgical instrument passing through a trocar during minimally invasive surgery, the surgical instrument having four DoFs.

FIG. 2 shows a surgical instrument 119 passing through a trocar 124 during minimally invasive surgery. For example, in case of laparoscopic surgery, this trocar 124 may be placed in the abdominal or thoracic wall, whereas in case of vitreoretinal surgery, the trocar 124 may be placed in the sclera. Rotating around and translating through the trocar may be possible in four DoF, e.g., the rotations ϕ 107, ψ 108, ϑ 110 and the translation z 109 to approach or penetrate a surgical target 123. Further shown are a tip 122 of the surgical instrument 119 and three axes 104-106 of a coordinate system fixed to the instrument tip, with $\vec{e}_z$ 106 aligned with the longitudinal axis of the surgical instrument 119. Rotations ϕ 107 and ψ 108 may result in a lateral displacement of the instrument tip 122, respectively in the direction $\vec{e}_y$ 105 and in the direction $\vec{e}_x$ 104. The translation z 109 may result in a longitudinal movement of the surgical instrument tip 122.

Figures 3, 4:
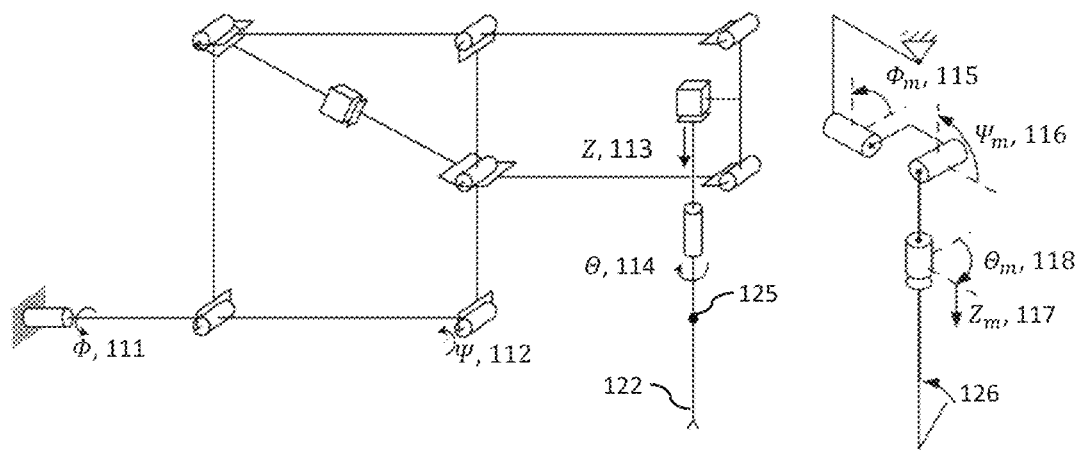
FIG. 3 shows a joint diagram illustrating the kinematics of a movable arm part of a surgical arm for use in minimally invasive surgery.
FIG. 4 shows a joint diagram illustrating the kinematics of a motion controller.

The surgical robotic system may be used in a minimally invasive procedure during minimally invasive surgery such as one of the abovementioned types. FIG. 3 shows a joint diagram illustrating the kinematics of a movable arm part of a surgical arm for use in such a minimally invasive surgery. In the example of FIG. 3, the surgical robotic system comprises a surgical arm, with the surgical arm comprising a movable arm part having DoFs $\Phi$ 111, $\Psi$ 112, Z 113 and $\Theta$ 114, allowing respective instrument motions 107-110, resulting in movements of the surgical instrument tip 122. The DoFs may be arranged such that there is a point on the surgical instrument that does not move in space, termed the Remote Center of Motion (RCM) 125. By moving the base of the surgical arm, the movable arm part may be positioned, such that its RCM 125 may be positioned at the trocar. Respective actuation units may be arranged to effect movement in all four DoFs 111-114.

The surgical robotic system may further comprise a human machine interface for receiving positioning commands from a human operator. The human machine interface may comprise or be constituted by a motion controller such as a joystick. FIG. 4 shows a joint diagram illustrating the kinematics of such a motion controller. Here, the motion controller is shown to have DoFs $\Phi_m$ 115, $\Psi_m$ 116, $Z_m$ 117 and $\Theta_m$ 118. The human operator may provide positioning commands by, e.g., holding the motion controller at a gripper part, pressing the button 126, and moving the gripper part of the motion controller in 3D space.

FIG. 5 shows a joint diagram illustrating the kinematics of a surgical arm having six revolutionary DoFs, thereby enabling longitudinal translation in z movement 109 of the surgical instrument towards a surgical target 123. The surgical robotic system may comprise a surgical arm with kinematics such that the same four movements are possible as those of the motion controller shown in FIG. 4. These kinematics need not contain a translational DoF, but might consist of 6 rotational DoFs in 3D space. 3D space may be indicated by coordinate system axis 101-103. Here, the DoFs are not arranged such that an RCM is kinematically constrained as in FIG. 3, but the processor may be configured for controlling the actuators of such 6 rotational DoFs so as to reflect the same four movements of the motion controller, i.e., establishing a software constrained RCM 125, and a longitudinal translation z 109 of the surgical instrument towards a surgical target 123. In addition, the processor may be configured for controlling the longitudinal movement 109 of the surgical instrument in accordance with the virtual bound. It will be appreciated that various other kinematic arrangements for surgical arms are possible which allow longitudinal translation of a surgical instrument, e.g., having another number of DoFs, incorporating, translational, prismatic, spherical joints or any other joints, etc.

As shown in FIG. 6, the surgical robotic system may also comprise a surgical arm with kinematics which enable longitudinal movement 109 of the surgical instrument, but without the DoFs or the processor being arranged such that an RCM is constrained. Such a surgical robotic system may be used in open surgery, where the instrument approaches a surgical target 123 from the outside, e.g., one which is located on a surface of an exterior of a patient. Here, the kinematics of the surgical arm in 3D space are indicated by coordinate system axis 101-103.

FIG. 7 shows a spherical virtual bound 132 being determined by a function of a furthest positioning of the surgical instrument as established by a human operator. Here, the term furthest positioning refers to a positioning that maximizes a virtual volume having a size determined by the positioning of the surgical instrument. It is noted that this function may be a linear or a non-linear function. Examples of a linear function are scaling of the furthest positioning, adding an offset, or establishing the virtual bound to correspond to the furthest positioning. An example of a non-linear function is resetting the virtual bound to its original location, e.g. when the instrument moves sufficiently away from the surgical target.

Here, the movable arm part has kinematics such that actuation may be possible in longitudinal direction 109, aligned with the longitudinal axis of the surgical instrument, and in at least two non-longitudinal directions, such as $\phi$ 107. The translation z 109 may be used for approaching the surgical target 123 from the outside. The translation z 109 may also be used for penetrating the surgical target 123 when the instrument is in contact with the surgical target 123, and may therefore be more demanding in terms of precision and steadiness compared to $\phi$ 107. The processor may be configured for establishing a spherical virtual bound 132 having a radius R 128 and a center at the RCM 125. The processor may be configured for determining the radius R 128 from the furthest positioning of the instrument in longitudinal direction 109, e.g., from all past positions of the instrument. In case of a new furthest position of the surgical instrument as established by the human operator, the virtual bound may be expanded 127.

Additionally or alternatively, the processor may be configured for in controlling the actuator, allowing longitudinal movement 109 of the surgical instrument towards the surgical target 123 past the virtual bound, subject to a positioning command being of a selected type, and updating 127 the virtual bound 132 based on a new furthest positioning. As such, the human operator may deliberately move the surgical instrument past the virtual bound, namely by providing suitable longitudinal positioning commands in positive z direction using the human machine interface. Here, the term z direction is a direction along the longitudinal axis of the surgical instrument, also indicated by the term longitudinal direction, a positive z direction refers to a direction towards the surgical target 123, and a negative z direction to a direction away from said target. Such positioning commands may be provided in separation of other types of positioning commands, e.g., using a different input mode or input modality of the human machine interface. In particular, such positioning commands may be of a selected type in that they cause the virtual bound 132 to be expanded by increasing the radius R 128.

FIG. 8 is similar to FIG. 7 but illustrates the use of a spherical virtual bound 132 with radius R 128, that is updated 127 based on positioning commands during minimally invasive surgery in a cavity of an organ in an interior of the patient. Here, the surgical instrument moves in z 109 and $\phi$ 107 directions, through the wall of the organ at the RCM 125, approaching the inside of a cavity in a (hollow) organ as the surgical target 123.

Figure 9:
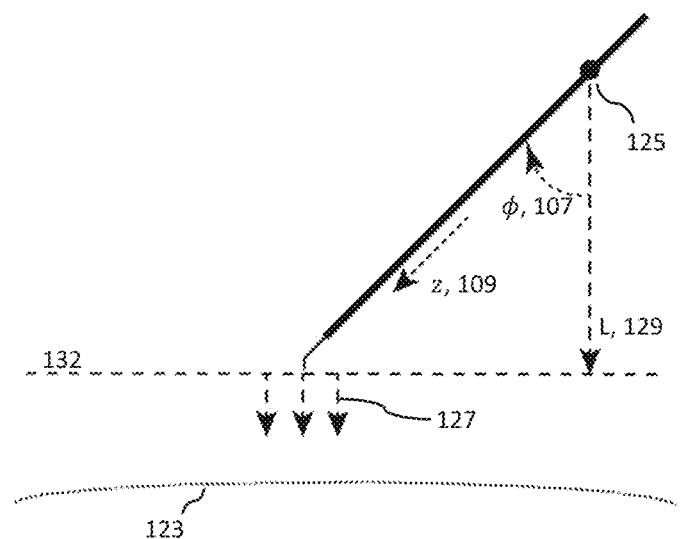
FIG. 9 shows a planar virtual bound.

As shown in FIG. 9, the virtual bound may also be a planar virtual bound 132, lying at a distance L 129, and with a preprogrammed orientation. The instrument may move in non-longitudinal direction 107 and in longitudinal direction z 109 to approach the surgical target 123. The processor may be configured to update 127 the distance L 129 such that all past instrument positions lie on the same side of the planar virtual bound 132 as the RCM 125.

It is noted that besides the virtual bound having a planar or spherical shape, many other surfaces and shapes may be used as virtual bound. Moreover, the virtual bound may be used in combination with any suitable kinematic arrangement of the surgical arm.

Figure 10:
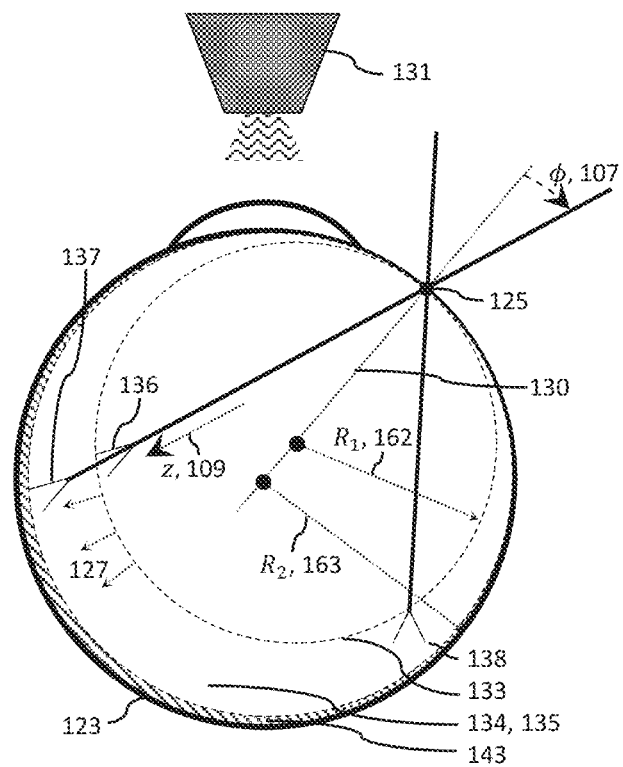
FIG. 10 illustrates the use of a spherical virtual bound during eye surgery.

FIG. 10 illustrates the use of a spherical virtual bound during eye surgery. The surgical instrument may move in longitudinal direction z 109 and in non-longitudinal direction ϕ 107. A spherical virtual bound is used with its center placed on the ϕ=0 line 130 and passing through the RCM 125. The radius of the spherical virtual bound may be updated by the processor, such that the spherical virtual bound comprises all previous instrument tip positions. Such configuration may be used for surgery at the inside of a hollow organ, such as eye surgery. FIG. 10 considers the case where the instrument penetrates the eye wall at the RCM 125. On responsibility of the human operator, the surgical instrument may be moved, namely by providing suitable positioning commands to the human machine interface. The position of the instrument tip at time $t_1$ 136 is at the virtual bound 133, which has radius $R_1$ at $t_1$ 162, and is moved in positive longitudinal direction z 109. By providing positioning commands of a selected type, the spherical virtual bound 133 may be enlarged 127 such that the instrument tip remains inside the spherical virtual bound. At time $t_2$, the human operator may visually confirm, e.g., using a microscope 131, that the instrument tip 137 is in (close) contact with the tissue on the inside of the eye. The human operator may not want to damage this tissue 123, and therefore may not advance or penetrate any further. Accordingly, the spherical virtual bound at time $t_2$ 134 with radius $R_2$ 163 may define zone A and zone B 143 within the eye. The position of the instrument tip at time $t_3$ 138 may be within zone A, and the virtual bound 134, 135 may therefore not be updated.

In general, the virtual bound may be established under responsibility and visual observation of the human operator. The processor may be configured for processing the positioning commands based on (the distance to) this bound. For example, zone A may be treated as a safe region, or a high-performance region within the eye, whereas zone B may be treated as a low-speed, high-precision region near delicate tissue.

Figure 11:
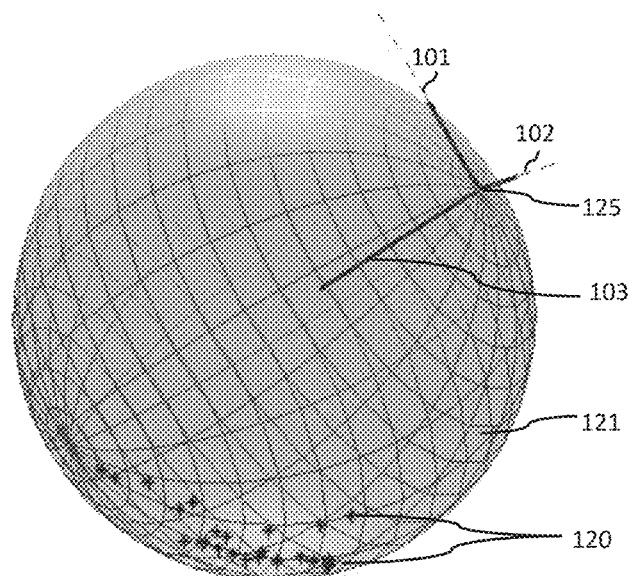
FIG. 11 shows the virtual bound being determined by an ellipsoid being fitted to multiple data points representing instrument positioning coordinates.

FIG. 11 shows the virtual bound being determined by an ellipsoid being fitted to multiple data points representing instrument positioning coordinates. Such instrument positioning coordinates may be represented, directly or indirectly, by the positioning commands provided by the human operator. As such, the processor may be configured for obtaining data points that represent the furthest instrument positioning coordinates on a grid distributed in space. In the previous figures, low order geometries, such as a plane or sphere, were used for the virtual bound defining zone A and B. However, also higher order shapes may be used, for example when it may be desirable to more accurately describe the geometry of a surgical target. During surgery, more data points may be obtained, e.g., when the instrument tip is moved to a different region, under responsibility and visual observation of the human operator. The surgical instrument may enter the eye at the RCM 125, therefore the coordinates (0,0,0) may be available as a data point. Using these data points, a virtual bound may be constructed, e.g., based on algebraic geometry or a numerical model. In the former case, the data points 120 may be used to fit a higher order algebraic geometry for the virtual bound 121, in 3D space 101-103. The algorithm used for fitting may minimize the volume of the geometry while enclosing all data points. As such, in the example of FIG. 11, an ellipsoid geometry may be chosen, since it may describe the eye's inner surface better than a sphere.

Figure 12:
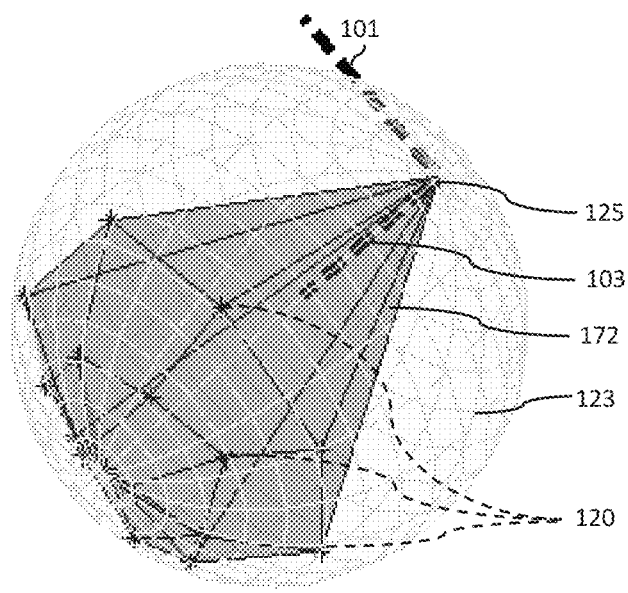
FIG. 12 illustrates a numerical model for the virtual bound being obtained by multiple data points being connected.

To fit a higher order algebraic geometry on a set of data points, a large number of data points may be desired. However, in case of an insufficient number of data points, geometry assumptions may not be correct and the fitting algorithm may encounter numerical difficulties. As an alternative, a numerical model for the virtual bound may be obtained by connecting multiple data points, as shown in FIG. 12. Namely, the data points 120 may be connected and interpolated to obtain a free-form surface in 3D space 101-103. In case the inner surface of the organ is non-convex, the volume 172 (zone A) may intersect the volume of the surgical target 123 in-between data points, when these data points are connected with straight lines. To avoid such intersection, more data points may be used on a finer grid, certain data points may be omitted or arcs (curving inwards) may be used to connect the data points. In this respect, it is noted that connecting the data point representing the RCM 125 to other data points with a straight line is allowed in case the surgical instrument is straight.

Figure 13:
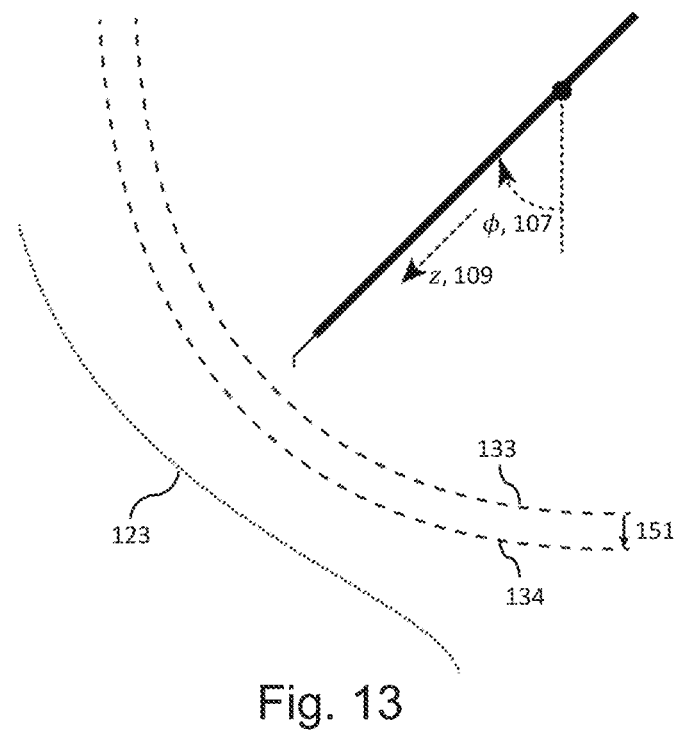
FIG. 13 shows the virtual bound being moved in a step-wise manner.

FIG. 13 illustrates the virtual bound being moved or expanded in a step-wise manner. Here, the movable arm part has the same kinematics z 109 and ϕ 107 and spherical virtual bound as in FIG. 7, but the virtual bound 133 may be incrementally expanded, e.g., with 50 μm 151, to obtain the new virtual bound 134. For that purpose, a different input mode or input modality may be used than for providing the positioning commands, e.g., using a foot pedal, a button, a touch-screen interface, etc. This approach of incrementally displacing, expanding or deforming the virtual bound, relative to the current bound position, size or shape, based on input provided through the human machine interface, may be super-positioned to the approach for determining the virtual bound based on the positioning commands, e.g., based on a furthest positioning established by the human operator. The human machine interface may also enable the human operator to displace the virtual bound relative to the current position of the instrument tip, instead of relative to the current virtual bound position. For example, by using a 'reset bound' button, the bound may be set to coincide with the current instrument tip location, or by using a second button, the virtual bound may be set to a predefined distance, e.g., 1 mm, from the instrument tip, in a z-direction 109 towards or from the surgical target 123.

Figure 14:
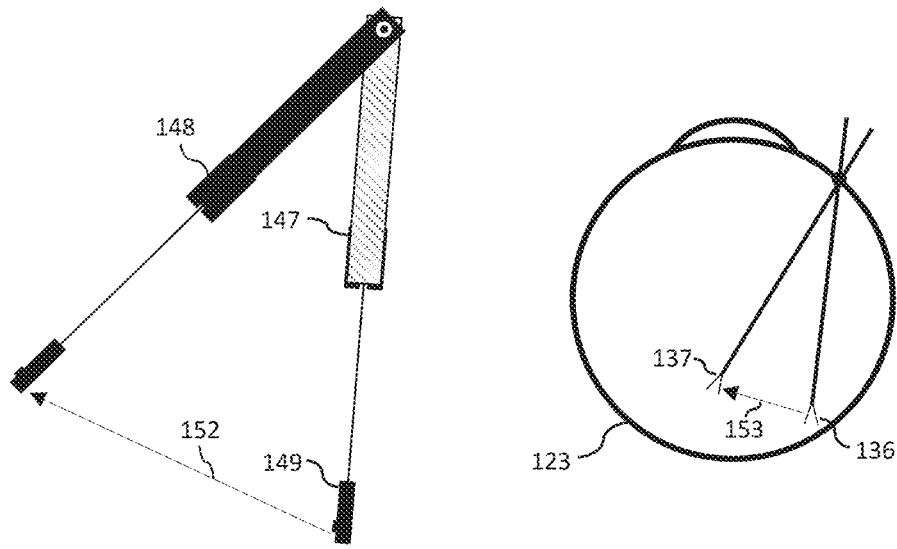
FIG. 14 shows a motion controller operating in a positioning mode.
Figure 15:
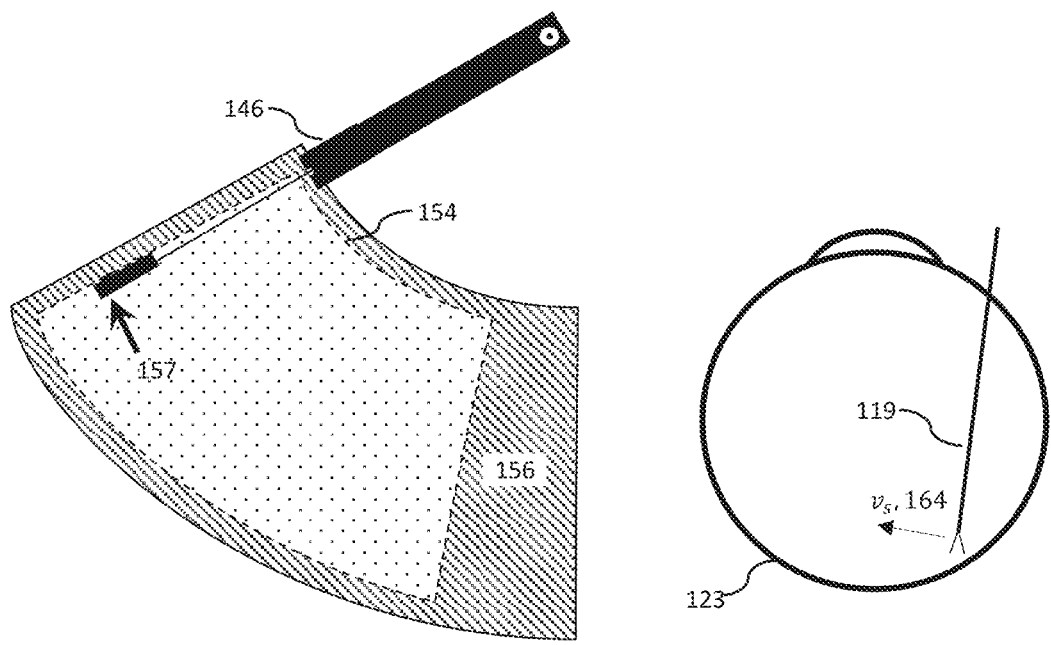
FIG. 15 shows a motion controller operating in a velocity mode.

FIGS. 14 and 15 relate to the human machine interface optionally comprising a motion controller having at least one DoF for enabling the human operator to provide the positioning commands by operating the motion controller within a workspace. The motion controller may be operable in a positioning mode in which the positioning commands are determined by a displacement of the motion controller within the workspace. The motion controller may also be operable in a velocity mode in which a positioning of the motion controller within a predetermined zone within the workspace is deemed to indicate a desired velocity, with the positioning commands being determined in accordance with the desired velocity. Here, the motion controller may have a translational DoF $Z_m$ 117, aligned with the longitudinal axis, and non-longitudinal DoFs, such as $\Phi_m$ 115 of FIG. 4.

FIG. 14 illustrates the positioning mode and FIG. 15 the velocity mode.

In the positioning mode of FIG. 14, the human operator may grab the motion controller 147 at the gripper part 149, and move it over a distance within its workspace, e.g., from position at time $t_1$ 147 to the position at time $t_2$ 148. The positioning command for the surgical instrument displacement $x_s$ 153 may be determined by the motion controller displacement $xc_m$, 152, using the relation $x_s = \alpha x_m$, where α is a (variable) scaling factor. This may result in an instrument movement from position 136 to position 137 with respect to the surgical target 123. In surgical procedures, a high precision may be desired, e.g., α<<1

In the velocity mode of FIG. 15, the motion controller 146 may be pushed 157 past a boundary in its workspace 156, termed the velocity mode boundary 154, to generate a desired surgical instrument velocity $v_s$ 164. The velocity may be a constant, or a function of the amount of displacement past the velocity mode boundary 154. The velocity may also be scaled with the (variable) scaling factor α, similarly to the positioning mode. The positioning command $x_s$ for the surgical instrument 119 for a new sample may be obtained by $x_s = \bar{x}_s + v_s \cdot dT$, where $\bar{x}_s$ is the positioning command from the previous sample, and dT is the time between samples.

It is noted that when the human operator wants to move the instrument tip over a large distance in positioning mode, especially in case of a small scaling factor α, the human operator may need to displace the motion controller 146 over a relatively long distance within the workspace 156. This may not be possible due to the limited size of the motion controller workspace 156. Moreover, the motion controller 146 may not be in a comfortable position for the human operator when it is moved to outer positions its workspace 156. The human operator may decouple the link between the movable arm part that holds the instrument and the motion controller, e.g. by releasing button 126. In decoupled mode, the instrument may stay at a fixed position, while the human operator may move the motion controller freely in its workspace, e.g. back to a comfortable position. Accordingly, to cover large distances in positioning mode, the human operator may use the technique of repeatedly coupling/decoupling: the human operator moves the motion controller in one direction while in coupled mode (button pressed) and in the other direction while in decoupled mode (button released).

The velocity mode may be more suitable to cover larger distances. The surgical instrument may move at a constant speed while the motion controller is kept stationary at the velocity mode boundary 154. Therefore, advantages of the velocity mode may include decreased user fatigue and faster task completion. However, the positioning mode may be safer than the velocity mode, because the human operator has to purposely move the motion controller to move the surgical instrument. Accordingly, the positioning commands provided in the velocity mode may be considered by the processor not to be of the selected type so as to disallow longitudinal movement of the surgical instrument towards the surgical target 123 past the virtual bound when the motion controller operates in the velocity mode. The processor may allow or disallow commands provided in the positioning mode or in the velocity mode, as a function of the virtual bound.

Figure 16:
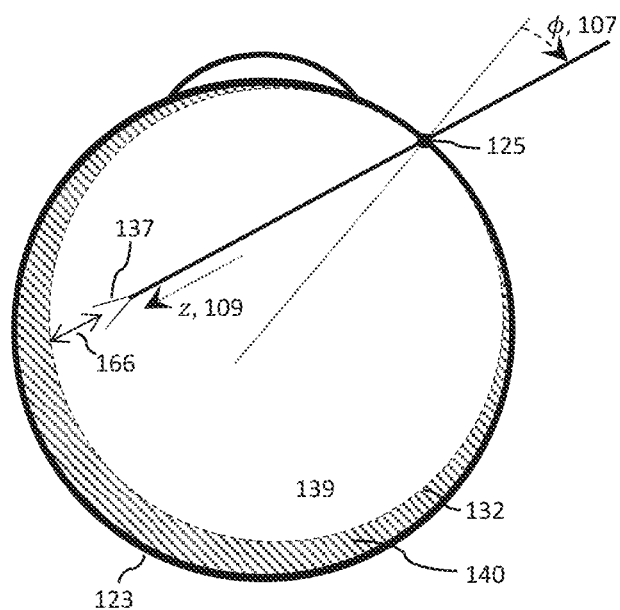
FIG. 16 illustrates longitudinal movement of the surgical instrument towards the surgical target past the virtual bound being disallowed in the velocity mode.

FIG. 16 illustrates this functionality, with the surgical instrument moving in z 109 and φ 107 around the RCM 125. Here, the spherical virtual bound 132 may be established as a linear or nonlinear function of previous furthest positions of the instrument tip at time $t_1$. This function may be a small offset in negative z-direction, e.g. 2 mm. The instrument at time $t_2$ 137 may be at a longitudinal distance 166 from the virtual bound. When the instrument tip moves from zone A past this virtual bound 132 into zone B 140, positioning commands provided in the velocity mode in the positive z-direction may be disallowed so as to disallow longitudinal movement of the surgical instrument towards the surgical target 123, whereas in the negative z-direction, they may be allowed. Positioning commands provided in the positioning mode may be allowed in zone B 140. This may be beneficial in that zone B 140 may be regarded as a low-speed, dangerous region near delicate tissue; hence the positioning mode may be more suitable. However, when the distance 166 is larger than zero, the human operator may use the velocity mode to quickly advance towards the virtual bound 132. In accordance with the above, the surgical instrument may then automatically stop at the virtual bound 132, because the velocity mode may not be allowed past the virtual bound.

Figure 17:
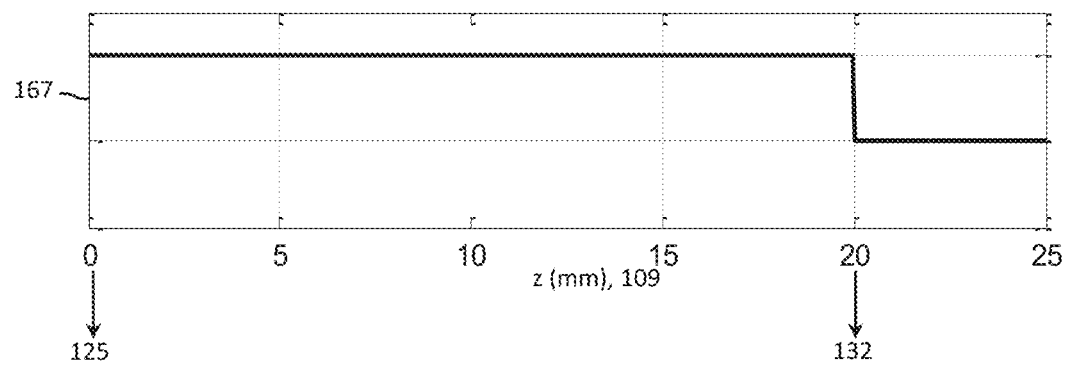
FIG. 17 shows the virtual bound being used in a scaling function.
Figure 18:
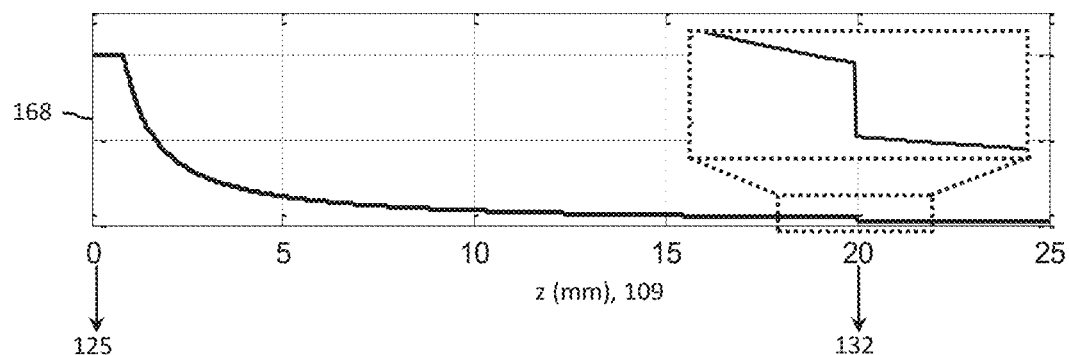
FIG. 18 shows the virtual bound being used in a function that determines the desired instrument velocity in a velocity mode of the motion controller.
Figure 19:
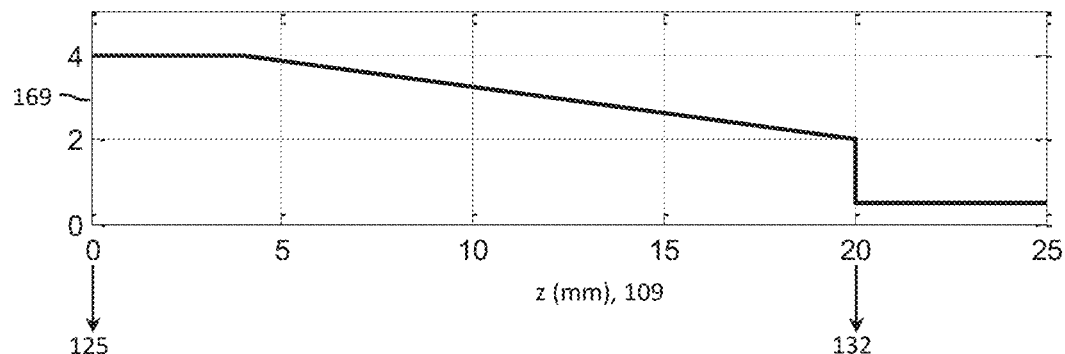
FIG. 19 shows the virtual bound being used in a frequency filter.

FIGS. 17-19 relate to the following. The processor may be configured for processing the positioning commands based on the virtual bound to obtain processed positioning commands, and using processed positioning commands in controlling the actuator. For example, the processing may comprise one or more of the group of: applying a scaling function, and applying a frequency filter, to the positioning commands. FIG. 17 shows the virtual bound being used in a scaling function. Here, the distance from the instrument tip to the virtual bound 132 may be used for the basis of a scaling function to determine the position scaling factor α, e.g., of the shape displayed in FIG. 17. This scaling function for a 167 may be relatively high when the position z 109 is in-between the RCM 125 and the virtual bound 132, resulting in fast instrument movements. When the instrument tip passes the virtual bound 132, a step in the scaling may occur, to a relatively low value for α, resulting in slower, more precise instrument movements. Alternatively, a smooth transition may be implemented. However, an advantage of a step may be that the human operator notices the passing of virtual bound 132, e.g., by observing the sudden slower instrument movement.

FIG. 18 shows the virtual bound being used in a function that determines the desired instrument velocity in a velocity mode of the motion controller. Here, another scaling function is shown. This scaling function 168 may be used to determine the desired surgical instrument velocity $v_s$ 164, in the velocity mode. In accordance with the scaling function, when the instrument tip is not deep inside the eye, the desired velocity $v_s$ is large, resulting in fast surgical instrument movements. When moving in z-direction 109 inside the eye, towards the virtual bound 132, $v_s$ is decreased as a function of the distance 166. When the instrument tip moves past the bound 132, $v_s$ is decreased by a large step.

FIG. 19 shows the virtual bound being used in a frequency filter. Here, another scaling function is shown, as a function of the longitudinal position z 109. This function may be used to determine the cut-off frequency 169 in a frequency filter that passes low frequencies and reduces the amplitude of signals with frequencies past this cut-off frequency 169. This frequency filter may be applied to the motion input signal $x_m$ 152, provided by the human operator, through the motion controller, to filter the human operator's hand tremor. In the example of FIG. 19, the cut-off frequency 169 decreases from 4 to 2 Hz, when the instrument approaches the virtual bound 132, resulting in smoother and slower instrument motions. When the instrument tip passes the virtual bound 132, a step decrease to 0.5 Hz occurs, being a convenient setting for delicate surgery, e.g., to the retina.

Figure 20:
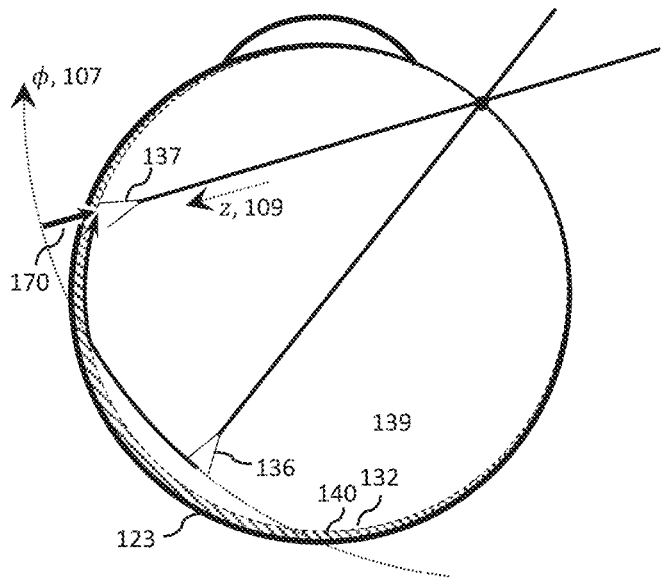
FIG. 20 shows the surgical instrument being retracted when non-longitudinal movement of the instrument causes the instrument to arrive at the virtual bound.

FIG. 20 shows the surgical instrument being retracted in longitudinal direction when non-longitudinal movement 107 of the instrument causes the instrument to arrive at the virtual bound. Here, the processor may be configured such that zone B 140 is regarded as a blocked zone. As such, longitudinal instrument penetration z 109 into zone B 140 may be disallowed. The human operator may move the instrument freely in zone A, but when the human operator provides a positioning command that would result in an instrument movement past the virtual bound 132, the positioning commands may be processed such that the instrument does not pass the virtual bound. This approach may be used to prevent accidental damage to delicate tissue 123 However, when observing the instrument tip and the delicate tissue, e.g., through a microscope, the human operator may purposely incrementally move the virtual bound, e.g., as described with reference to FIG. 13 by pressing a foot pedal. This may enable the human operator to carefully advance or penetrate further in z direction, in a very controlled and defined manner. It is noted that in general, the human machine interface might provide means to disregard the virtual bound, e.g., a specific input mode or input modality, and continue free positioning of the instrument, including penetration in z direction.

However, as shown in FIG. 20, the instrument may also move into zone B by a non-longitudinal movement 107. In such cases where the virtual bound is a plane or contour in 3D, the processor may be configured for controlling the actuator to retract the surgical instrument causing the surgical instrument to arrive at the plane or the contour. In the example of FIG. 20, the instrument tip position at time $t_1$ 136 is in zone A 139, but it is moving towards zone B because the human operator is providing positioning commands in the direction φ 107. Because movement into zone B may be disallowed, the positioning commands for z may be processed such that the instrument may move along the virtual bound 132. Effectively, by suitably retracting the surgical instrument, the instrument tip position at time $t_2$ 137 may be corrected in z direction over a distance 170, such that movement of the surgical instrument into zone B, towards, or further into the surgical target 123, is avoided.

Figure 21:
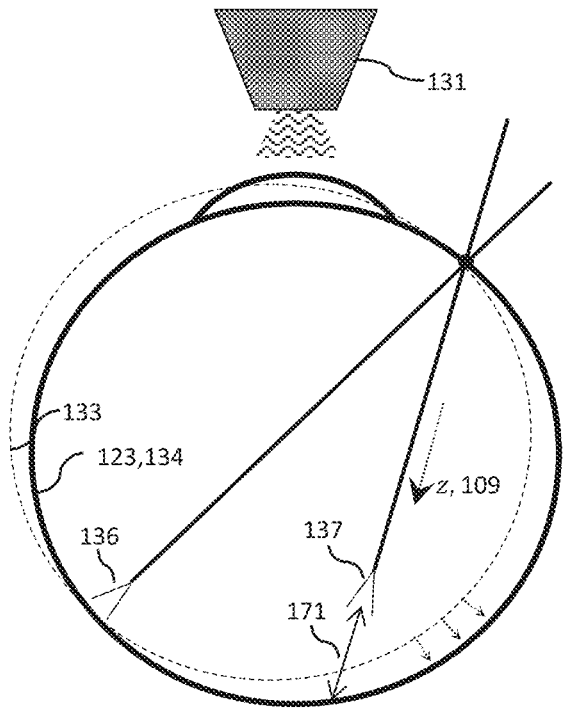
FIG. 21 shows the virtual bound being updated or replaced, based on sensor data indicating a distance to the surgical target.

FIG. 21 shows the virtual bound being repositioned, expanded or deformed, based on sensor data indicating a distance to the surgical target. Here, the virtual bound 133 may be established by a previous furthest positioning of the instrument tip at time $t_1$ 136. However, the virtual bound does not coincide with the surgical target 123, being in this case the retina on the inside of an eye. A reason for this may be that the surgical target may have been rotated, moved or deformed, or the shape of the virtual bound is not representing the organ's geometry correctly. However, the surgical robotic system may comprise a sensor inside or outside the eye which measures the longitudinal distance 171 between the instrument tip 137 and the surgical target. The sensor may obtain measurement data points, similar to those described with reference to FIGS. 11 and 12. The sensor data may be used to update the virtual bound such that the virtual bound at time $t_2$ 134 coincides with the surgical target 123. This updating may comprise repositioning, expansion or deformation of the virtual bound.

The longitudinal distance 171 may be measured indirectly, by a sensor outside the eye such as a camera or an optical coherence tomography device mounted on a microscope 131, with a view on the surgical target and the surgical instrument tip 137, through the pupil.

Indirect measurement may also be done by a sensor in the eye, mounted on another instrument or positioned in the eye by other means. The longitudinal distance 171 may also be measured directly, by a sensor added to the surgical instrument and measuring along the z-direction 109. The sensor may be a non-contact distance sensor providing optical coherence tomography through an optical fiber, integrated in or attached to the surgical axis. However, this is not a limitation, in that also other non-contact distance sensors may be used, e.g., based on other optical principles, or sensors based on acoustical or electrical principles. In general, such types of distance sensor may provide an output, i.e., sensor data, proportional to the distance over a certain range of positions.

Additionally or alternatively, a proximity switch sensor may be used. Here, the distance 171 is not measured over a range, but the presence of the surgical target within a position threshold is detected, e.g., at a distance of 0.1 mm. If the threshold is 0 mm, the sensor acts as a contact/no-contact sensor. The coordinates of the instrument tip may now be a measure of the surgical target position. Having obtained these sensor data, the processor may update or replace the virtual bound 132.

It is noted that, in updating or replacing the virtual bound based on sensor data, more samples may be used than only the current sample of the sensor data. Namely, due to possible noise and uncertainty in this data, also previous samples of sensor data may be used, and/or previous positions of the virtual bound position. For example, the virtual bound may be updated using a Kalman filter to account for noise and uncertainty in the sensor data.

Figure 22:
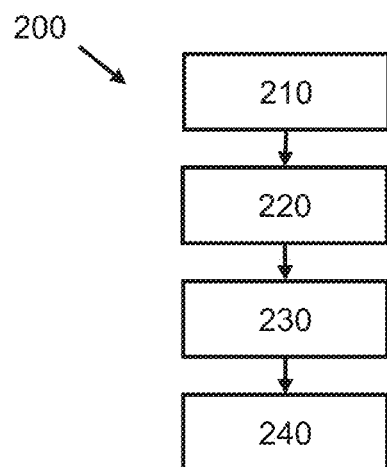
FIG. 22 schematically shows a method for controlling a surgical robotic system during use in a surgical procedure.

FIG. 22 schematically illustrates a method 200 for controlling a surgical robotic system during use in a surgical procedure, the surgical robotic system comprising a surgical arm, the surgical arm comprising a movable arm part, the movable arm part comprising an instrument connector for mounting of a surgical instrument, the surgical instrument having a longitudinal axis, the movable arm part having at least one DoF to enable longitudinal movement of the surgical instrument along the longitudinal axis of the surgical instrument towards a surgical target. The method 200 comprises, in an operation titled "RECEIVING POSITIONING COMMANDS", receiving 210 positioning commands from a human operator for controlling the longitudinal movement of the surgical instrument. The method 200 further comprises, in an operation titled "ACTUATING MOVABLE ARM PART", actuating 240 the movable arm part to effect the longitudinal movement of the surgical instrument. The method 200 further comprises, in an operation titled "CONTROLLING THE ACTUATING", controlling 230 said actuating in accordance with the positioning commands and a virtual bound, the virtual bound establishing a transition in the control of the longitudinal movement of the surgical instrument in a direction towards the surgical target. The method 200 further comprises, in an operation titled "DETERMINING VIRTUAL BOUND", during use of the surgical robotic system in the surgical procedure, determining 220 the virtual bound based on the positioning commands. It is noted that the operations of the method 200 may be performed in any suitable order. The method 200 may be performed iteratively.

Figure 23:
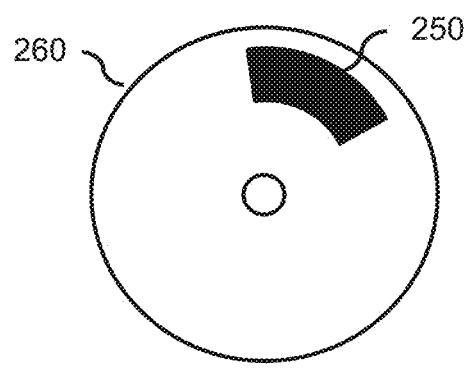
FIG. 23 shows a computer program product comprising instructions for causing a processor system to perform the method.

The method according to the invention may be implemented on a processor as a computer implemented method, or in dedicated hardware, or in a combination of both. Executable code for a method according to the invention may be stored on a computer program product. Examples of computer program products include memory devices, optical storage devices, integrated circuits, servers, online software, etc. FIG. 23 shows a computer program product in the form of an computer readable medium 260 which comprises non-transitory program code 250 for causing a processor to perform a method according to the invention when said program code is executed the processor.

In a preferred embodiment, the computer program comprises computer program code means adapted to perform all the steps of a method according to the invention when the computer program is executed by a processor. Preferably, the computer program is embodied on a computer readable medium.

It should be noted that the above-mentioned embodiments illustrate rather than limit the invention, and that those skilled in the art will be able to design many alternative embodiments.

In the claims or clauses, any reference signs placed between parentheses shall not be construed as limiting the claim or clause. Use of the verb "comprise" and its conjugations does not exclude the presence of elements or steps other than those stated in a claim or clause. The article "a" or "an" preceding an element does not exclude the presence of a plurality of such elements. The invention may be implemented by means of hardware comprising several distinct elements, and by means of a suitably programmed computer. In the device claim or clause enumerating several means, several of these means may be embodied by one and the same item of hardware. The mere fact that certain measures are recited in mutually different dependent claims or clauses does not indicate that a combination of these measures cannot be used to advantage.

The invention claimed is:

1. A surgical robotic system for use in an eye surgery procedure, comprising:
   a surgical arm comprising a movable arm part, the movable arm part comprising an instrument connector for mounting of a surgical instrument, the surgical instrument having a longitudinal axis, the movable arm part having at least one degree-of-freedom to enable longitudinal movement of the surgical instrument along the longitudinal axis of the surgical instrument towards a surgical target within an eye;
   a human machine interface for receiving positioning commands from a human operator for controlling the longitudinal movement of the surgical instrument;
   an actuator configured and arranged for actuating the movable arm part to effect the longitudinal movement of the surgical instrument;
   a processor configured for controlling the actuator in accordance with the positioning commands and a virtual bound, the virtual bound dividing physical space towards the surgical target into at least a first zone and a second zone;
   wherein the surgical instrument comprises a sensor for providing sensor data, the sensor data being indicative of a distance between a tip of the surgical instrument and an anatomical structure;
   wherein the processor is further configured for:
      during use, determining the virtual bound based on the sensor data; and
      establishing a transition in control behavior based on the virtual bound by controlling the actuator differently for positioning commands representing longitudinal movement of the surgical instrument in or in a direction of the second zone than for positioning commands representing longitudinal movement of the surgical instrument in or in a direction of the first zone.

2. The surgical robotic system according to claim 1, wherein the processor is configured to apply a scaling function or a frequency filter to the positioning commands to obtain processed positioning commands and to control the actuator based on the processed positioning commands.

3. The surgical robotic system according to claim 2, wherein the scaling function or the frequency filter causes a different processing of positioning commands representing longitudinal movement of the surgical instrument in or in the direction of the second zone than positioning commands representing longitudinal movement of the surgical instrument in or in the direction of the first zone.

4. The surgical robotic system according to claim 2, wherein the scaling function or the frequency filter comprises a parameter which is dependent on the distance between the tip of the surgical instrument and the virtual bound.

5. The surgical robotic system according to claim 4, wherein the scaling function comprises a scaling factor for causing a desired longitudinal movement or longitudinal velocity of the surgical instrument, as indicated by the positioning commands, to be scaled in accordance with the scaling factor, wherein the scaling factor is the parameter which is dependent on the distance between the tip of the surgical instrument and the virtual bound.

6. The surgical robotic system according to claim 5, wherein the scaling factor is smaller for positioning commands representing longitudinal movement of the surgical instrument in or in the direction of the second zone than for positioning commands representing longitudinal movement of the surgical instrument in or in the direction of the first zone.

7. The surgical robotic system according to claim 4, wherein the frequency filter comprises a cut-off frequency as the parameter which is dependent on the distance between the tip of the surgical instrument and the virtual bound.

8. The surgical robotic system according to claim 7, wherein the cut-off frequency is lower for positioning commands representing longitudinal movement of the surgical instrument in or in the direction of the second zone than for positioning commands representing longitudinal movement of the surgical instrument in or in the direction of the first zone.

9. The surgical robotic system according to claim 1, wherein the processor is configured to control the actuator to dampen or disallow longitudinal movement of the surgical instrument towards the surgical target past the virtual bound.

10. The surgical robotic system according to claim 1, wherein the processor is configured to control the actuator to retract the surgical instrument in longitudinal direction when movement of the instrument causes the instrument to arrive past the virtual bound.

11. The surgical robotic system according to claim 1, wherein the human machine interface comprises a motion controller having at least one degree-of-freedom for enabling the human operator to provide the positioning commands by operating the motion controller within a workspace.

12. The surgical robotic system according to claim 11, wherein the motion controller is operable in a positioning mode in which the positioning commands are determined by a displacement of the motion controller within the workspace.

13. The surgical robotic system according to claim 11, wherein the motion controller is operable in a velocity mode in which a positioning of the motion controller within a predetermined zone within the workspace is deemed to indicate a desired velocity, with the positioning commands being determined in accordance with the desired velocity.

14. The surgical robotic system according to claim 11, wherein the motion controller is a joystick.

15. The surgical robotic system according to claim 1, wherein the virtual bound is spherical or an ellipsoid.

16. The surgical robotic system according to claim 1, wherein the processor is configured for controlling the actuator to always allow longitudinal movement of the surgical instrument away from the surgical target.

17. The surgical robotic system according to claim 1, wherein the sensor is a non-contact distance sensor providing optical coherence tomography through an optical fiber which is integrated in or attached to the surgical axis of the surgical instrument.

18. A method for controlling a surgical robotic system during use in an eye surgery procedure, the surgical robotic system comprising a surgical arm, the surgical arm comprising a movable arm part, the movable arm part comprising an instrument connector for mounting of a surgical instrument, the surgical instrument having a longitudinal axis, the movable arm part having at least one degree-of-freedom to enable longitudinal movement of the surgical instrument along the longitudinal axis of the surgical instrument towards a surgical target within an eye, the method comprising:

receiving positioning commands from a human operator for controlling the longitudinal movement of the surgical instrument;

actuating the movable arm part to effect the longitudinal movement of the surgical instrument;

controlling said actuating in accordance with the positioning commands and a virtual bound, the virtual bound dividing physical space towards the surgical target into at least a first zone and a second zone;

wherein the surgical instrument comprises a sensor for providing sensor data, the sensor data being indicative of a distance between a tip of the surgical instrument and an anatomical structure;

the method further comprising:

during use of the surgical robotic system in the surgical procedure, determining the virtual bound based on the sensor data; and establishing a transition in the control behavior based on the virtual bound by controlling the actuator differently for positioning commands representing longitudinal movement of the surgical instrument in or in a direction of the second zone than for positioning commands representing longitudinal movement of the surgical instrument in or in a direction of the first zone.

19. A computer-readable medium comprising non-transitory data representing a computer program, the computer program comprising instructions for causing a processor system to perform the method according to claim 18.

* * * * *